United States Patent
Gonzalez

(10) Patent No.: US 11,039,819 B2
(45) Date of Patent: Jun. 22, 2021

(54) NEEDLE HANDLE

(71) Applicant: Spiration Inc., Redmond, WA (US)

(72) Inventor: Hugo X. Gonzalez, Woodinville, WA (US)

(73) Assignee: GYRUS ACMI, INC., Westborough, MA (US)

( * ) Notice: Subject to any disclaimer, the term of this patent is extended or adjusted under 35 U.S.C. 154(b) by 814 days.

(21) Appl. No.: 15/693,070

(22) Filed: Aug. 31, 2017

(65) Prior Publication Data

US 2019/0059864 A1 Feb. 28, 2019

(51) Int. Cl.
*A61B 10/02* (2006.01)
*A61M 5/32* (2006.01)
*A61M 5/34* (2006.01)
*A61M 5/50* (2006.01)

(52) U.S. Cl.
CPC ....... *A61B 10/0283* (2013.01); *A61M 5/3202* (2013.01); *A61M 5/329* (2013.01); *A61M 5/34* (2013.01); *A61M 5/5086* (2013.01); *A61M 2205/581* (2013.01); *A61M 2205/582* (2013.01)

(58) Field of Classification Search
None
See application file for complete search history.

(56) References Cited

U.S. PATENT DOCUMENTS

| | | | |
|---|---|---|---|
| 5,601,588 A * | 2/1997 | Tonomura | A61B 10/04 606/181 |
| 2002/0108614 A1* | 8/2002 | Schultz | A61M 1/0047 128/207.14 |
| 2008/0051711 A1* | 2/2008 | Mounce | A61J 1/1406 604/131 |
| 2009/0204005 A1* | 8/2009 | Keast | A61B 8/12 600/461 |
| 2013/0053726 A1* | 2/2013 | Miller | A61B 10/0275 600/567 |
| 2014/0094758 A1* | 4/2014 | Jugl | A61M 5/3202 604/198 |
| 2015/0238699 A1* | 8/2015 | Butler | A61M 5/3158 604/228 |

* cited by examiner

*Primary Examiner* — Jacqueline Cheng
*Assistant Examiner* — Tho Q Tran
(74) *Attorney, Agent, or Firm* — Clements Bernard Walker; Michael S. Smith

(57) ABSTRACT

A medical instrument having an aspiration and/or injection needle and handle device. The handle device provides audible and/or tactile feedback during the application of activation forces, thus enabling the user to determine where the distal end of the aspiration and/or injection needle is relative to a sheath. More than two grooves are present on a shaft of an activation handle of the handle device. An O-ring resides within a handle portion of the handle device. The O-ring seats and unseats within the grooves based on the amount of applied force.

12 Claims, 7 Drawing Sheets

NEEDLE HANDLE

FIELD

The present invention relates to needle aspiration devices used for tissue sampling.

BACKGROUND

The statements in this section merely provide background information related to the present disclosure and may not constitute prior art.

Needle aspiration devices, such as transbronchial needle aspiration (TBNA) devices, are used to collect samples from target tissue, such as lymph nodes, tumors and nodules, for analysis. In some cases, these needles are used to inject substances.

Some needle handle designs use simple cantilever springs, friction fits or O-rings. The earlier O-ring designs offer some "locking" ability with a groove to seat the O-ring. However, those grooves are generally shallow, which could also allow the needle to accidentally advance without the user's input, causing a potential safety issue or scope damage.

SUMMARY

The present invention provides an example medical instrument for sampling tissue and/or injecting substances into tissue. The example medical instrument includes a needle, a needle actuator, a shaft section and a lumen located within one of the actuator section or the shaft section.

The needle actuator includes an actuator section located at a proximal end of the needle actuator. The shaft section includes at least three annular grooves. The lumen securably receives the proximal end of the needle. The sheath includes a lumen configured to receive the needle. The handle body includes a distal end and a proximal end, where the distal end of the handle body is coupled to the proximal end of the sheath. The handle body includes a lumen, an annular groove within the lumen of the handle body and an O-ring at least partially received by the annular groove of the handle body. The at least three annular grooves allow the O-ring to at least partially seat when the respective annular groove is collocated with the annular groove within the lumen of the handle body. The multiple grooves allow a physician to extend the needle at defined distance stages, thus giving the physician more knowledge about where the tip of the needle is relative to the end of the sheath.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1-2 illustrates an side view of the aspiration device of FIG. 1-1 in an activated state in accordance with principles of the present invention;

FIG. 1-3 illustrates a cross-sectional view of the aspiration device of FIG. 1-1;

FIG. 2-1 illustrates a side view of a needle actuator of the aspiration device of FIG. 1-1 in accordance with principles of the present invention;

FIG. 2-2 illustrates a close-up view of a portion of the needle actuator of FIG. 2-1;

FIG. 3-1 illustrates a side view of a handle body of the aspiration device of FIG. 1-1 in accordance with principles of the present invention;

FIG. 3-2 illustrates a cross-sectional view of the handle body of FIG. 3-1;

FIG. 3-3 illustrates a cross-sectional view of a portion of the handle body of FIGS. 3-1 and 3-2;

FIG. 4-1 illustrates an side view of an aspiration device in a deactivated state in accordance with principles of the present invention;

FIG. 4-2 illustrates an side view of the aspiration device of FIG. 4-1 in an activated state in accordance with principles of the present invention;

FIG. 4-3 illustrates a cross-sectional view of the aspiration device of FIG. 4-1.

DETAILED DESCRIPTION

The following description is merely exemplary in nature and is not intended to limit the present disclosure, application, or uses.

Figure 1:
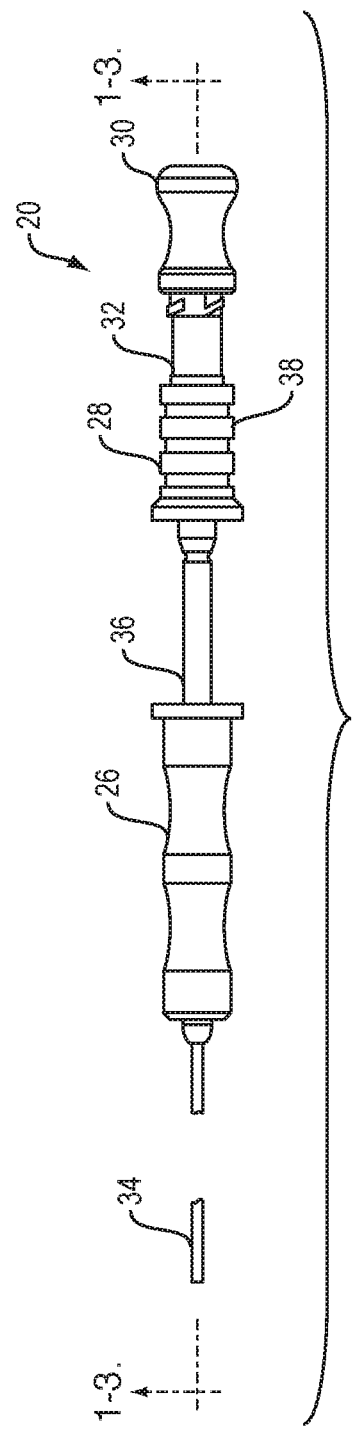
FIG. 1-1 illustrates an side view of an aspiration device in a deactivated state in accordance with principles of the present invention.
Figures 1, 2:
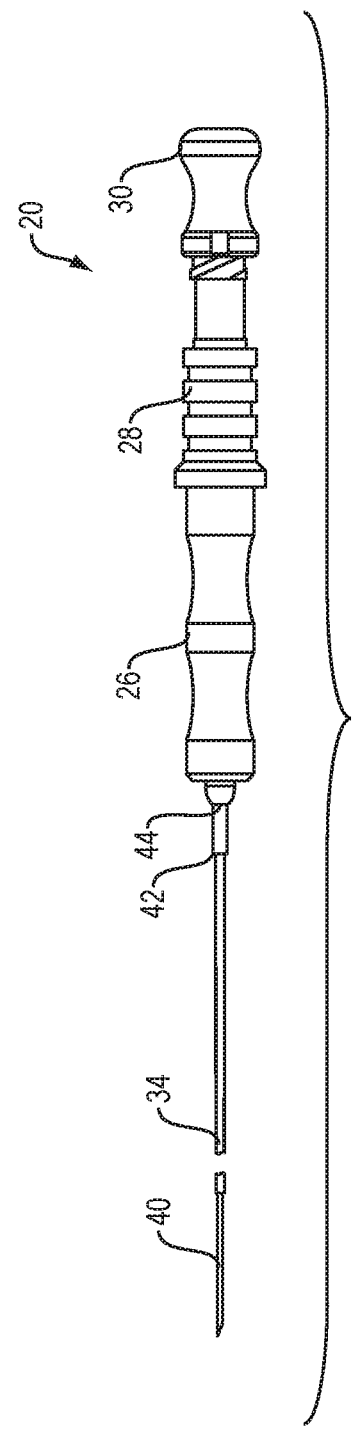
Figures 1, 2, 3:
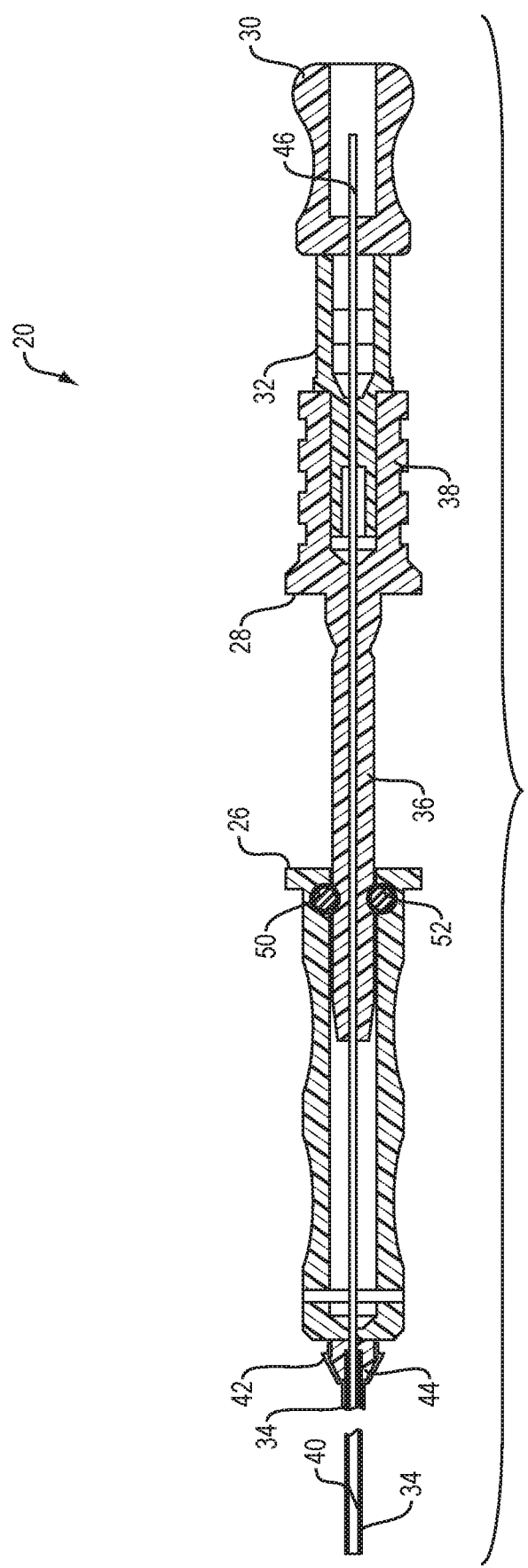
Figures 1, 2:
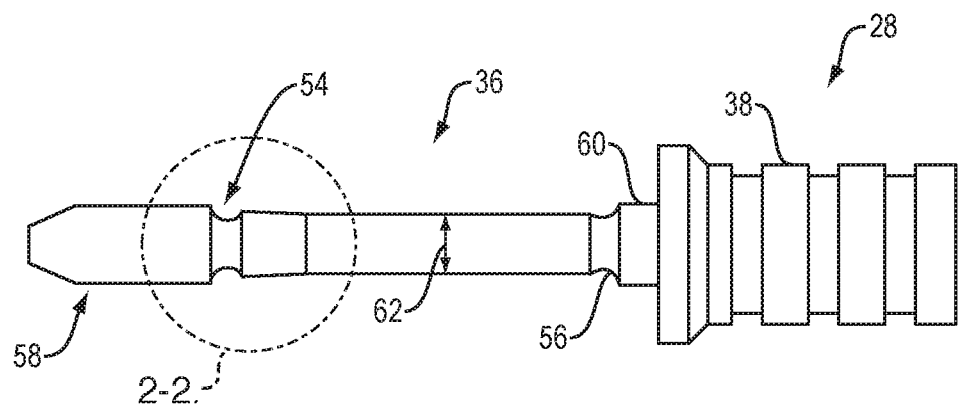
Figure 2:
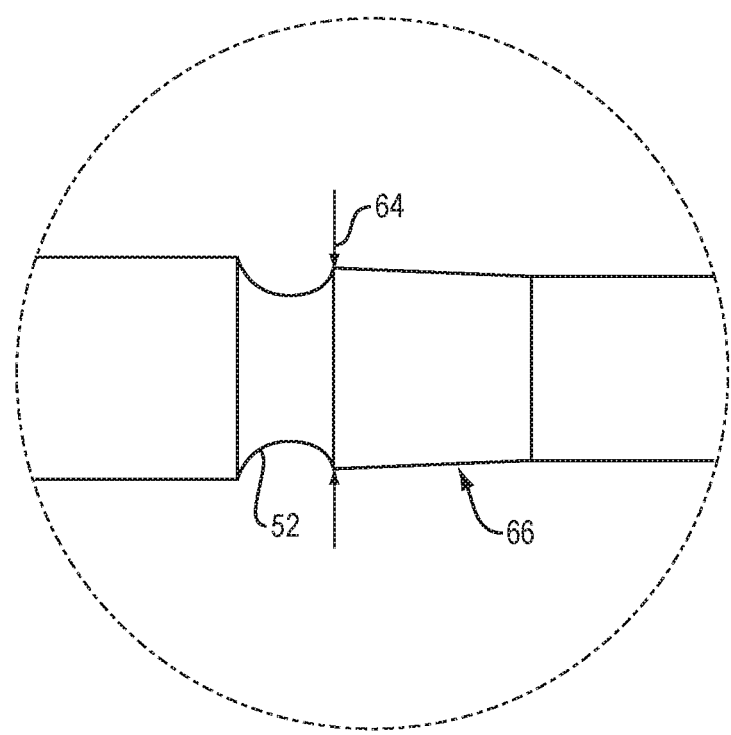
Figures 1, 3:
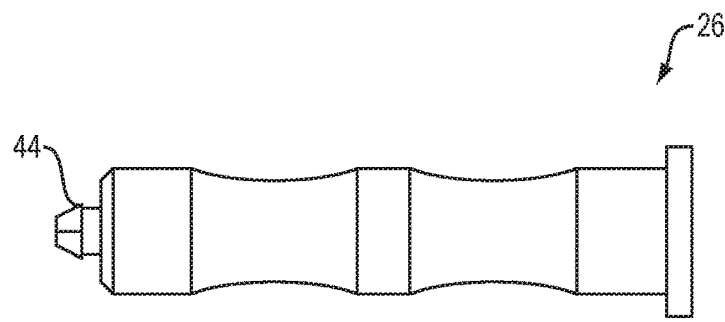
Figures 2, 3:
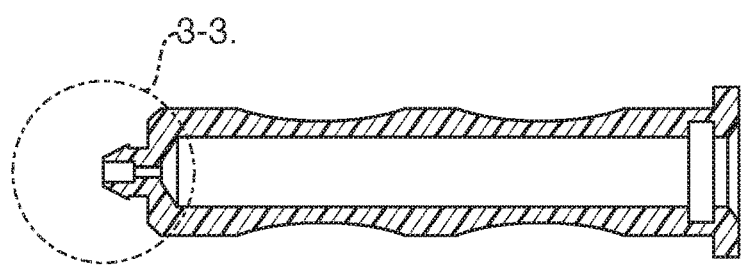
Figure 3:
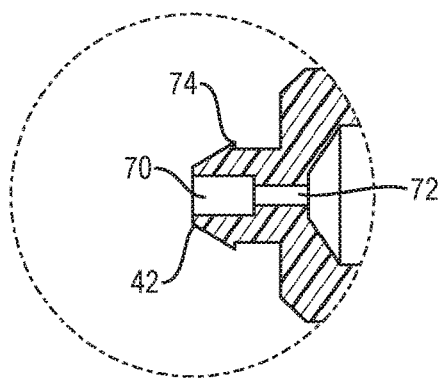

FIGS. 1-1 and 1-3 illustrate an example needle aspiration device 20 (e.g., transbronchial needle aspiration (TBNA) device) in a deactivated position and FIG. 1-2 illustrates the device 20 in an activated position. The device 20 includes a handle body 26, a needle actuator 28, a stylet knob 30 and a Luer component 32. The handle body 26 is attached to a proximal end of a sheath 34. The needle actuator 28 includes a shaft portion 36 coupled to a handle portion 38. The needle actuator 28 receives and is attached to a proximal end of a needle 40. The stylet knob 30 is attached to a proximal end of a stylet 46. The stylet knob 30 rotatably receives to a proximal end of the Luer component 32. A distal end of the Luer component 32 is attached to a cavity of the handle portion 38 of the needle actuator 28.

In the deactivated position, the distal end of the needle 40 is retracted within the sheath 34 (FIG. 1-3). In the activated position, the distal end of the needle 40 is exposed beyond the distal end of the sheath 34 (FIG. 1-2).

As shown in FIG. 1-3, the shaft portion 36 is slidably received within a cavity (i.e., lumen) of the handle body 26. At a proximal end of the cavity of the handle body 26 is an annular groove 52 that receives at least a portion of an O-ring 50. The O-ring 50 keeps the shaft portion 36 from being easily removed from the handle body 26. Interactive operation of the parts of the device 20 are described in more detail below.

As shown in FIGS. 2-1 and 2-2, the shaft portion 36 of the needle actuator 28 includes a distal section 58, a middle section 62 and a proximal section 60. The distal section 58 and the middle section 62 are separated by a distal annular groove 54. The middle section 62 and the proximal section 60 are separated by a proximal annular groove 56. The distal section 58 has an outside diameter that is approximately the same as the inside diameter of the cavity of the handle body 26. As part of assembly, the shaft portion 36 is inserted into the cavity of the handle body 26. The distal section 58 is forced past the O-ring 50 until the O-ring 50 becomes seated within the distal annular groove 54. At this position, the device 20 is ready for operation with the distal end of the needle 40 being proximal to the distal end of the sheath 34. The O-ring 50 prevents the distal section 58 of the needle actuator 28 from being completely pulled out of the handle body 26.

A user initiates needle activation by applying a distal force on the handle portion 38 of the needle actuator 28 thus causing the O-ring 50 to pop out of the distal annular groove 54 and slide along the shaft portion 36 until the O-ring 50 'pops' into place at the end (e.g., the proximal annular groove 56), at which point the needle is fully extended (e.g., about 20 mm) from the sheath 34.

A ramp 66 is located from the proximal edge of the distal annular groove 54 to a predefined location proximally along the shaft portion 36. The outside diameter 64 of the ramp 66 decreases from the proximal edge of the distal annular groove 54 to a proximal end of the ramp 66. The shaft portion 36 located between the proximal end of the ramp 66 and the proximal annular groove 56 has a mostly constant diameter value. The value of the diameter of the distal end of the ramp 66 is chosen in order to provide audible and/or tactile feedback to the operator as the operator applies an initiation force to the needle actuator 28 in the distal direction. The ramp 66 provides for an asymmetric force difference between the activation force, which is relatively sudden and noticeable, and the retraction force, which is smoother and subtler than the activation force.

The distal section 60 may have a diameter value that is greater than the non-ramp portion of the middle section 62. The O-ring 50 seated into the proximal annular groove 56 helps to keep the needle actuator 28 in a fully distal position. The device 20 may be implemented without the distal section 60 or the distal annular groove 54.

In one embodiment, the distal annular groove 54 is slightly deeper than the proximal annular groove 56. This helps to keep the needle 40 locked in a retracted position until physician initiated activation occurs. The distal annular groove 54 may be flanked by a slope on a proximal side and a sharper, wider end on the distal side. The wider side making contact with the O-ring 50 prevents the actuator from being completely pulled out from the handle body 26.

Other shapes and dimensions for the device 20 may be used, including intermediate ramps or divots, to vary the activation force and feel during use. For instance a notch or bump at a half-way point between zero and full activation may be used to provide physicians with feedback about the location of the midway point.

As shown in FIGS. 3-1, 3-2 and 3-3, a barb 44 is located at the distal end of the handle body 26. The barb 44 includes a distal cavity 70 and a proximal cavity 72. The proximal cavity 72 has a smaller inside diameter than the distal cavity 70 but is still large enough to slidably receive the needle 40. The distal cavity 70 is sized to receive a proximal end of the sheath 34 up to a shelf formed due to the diameter disparity between the distal cavity 70 and the proximal cavity 72. The barb 44 includes a tapered distal end that expands proximally until about midway the length of the barb 44 where a flange 74 is formed. The shaft of the barb 44 has a constant outside diameter from the tapered distal end to the distal end of the handle body 26. The flange 74 allows for greater adhesion to a strain relief liner 42.

After the sheath 34 has been inserted into the distal cavity 70, the strain relief liner 42 is drawn or applied over the sheath 34 and the barb 44. If the strain relief liner 42 is formed at least partially of heat shrink material, heat is applied to it, thus causing it to shrink and apply radial forces to the sheath 34 and the barb 44. The heat shrink material may include an adhesive located on its inner surface for allowing for greater adhesion between the parts. This adhesive may also be heat activated.

Figures 1, 4:
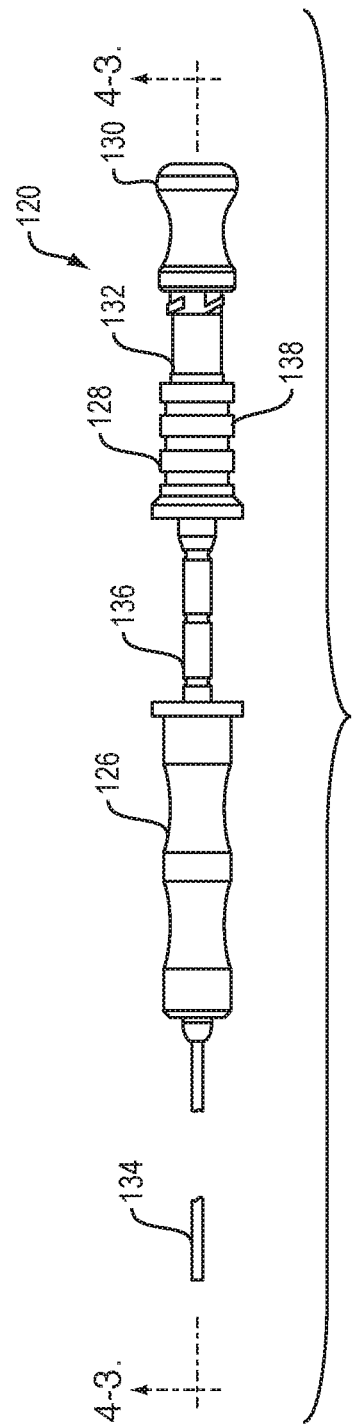
Figures 2, 4:
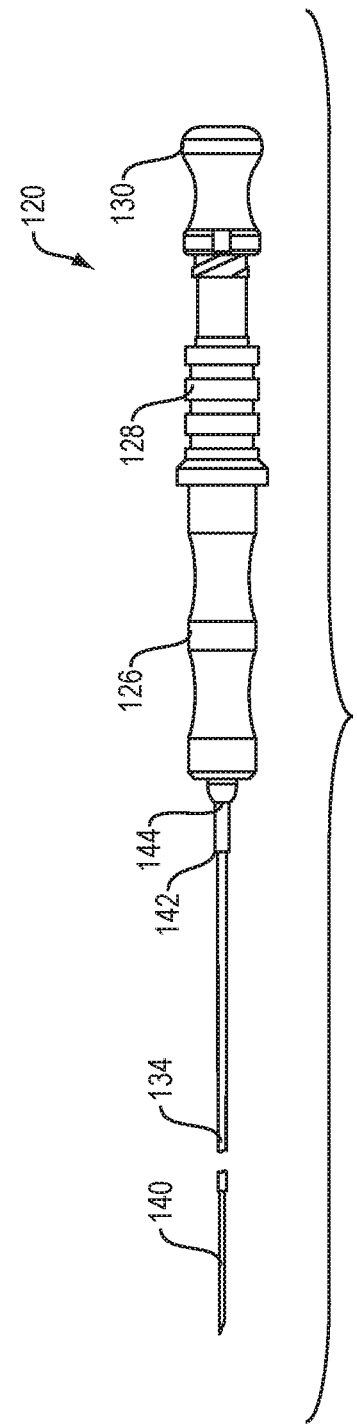
Figures 3, 4:
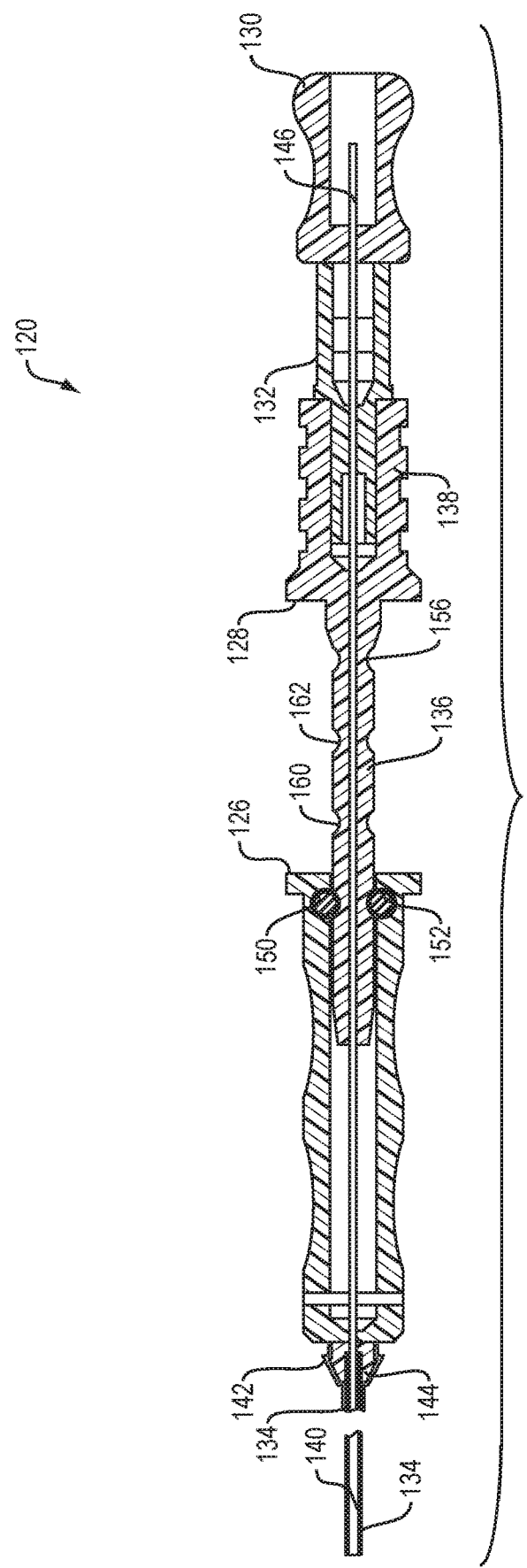

FIGS. 4-1 and 4-3 illustrate an example needle aspiration device 120 (e.g., transbronchial needle aspiration (TBNA) device) in a deactivated position and FIG. 4-2 illustrates the device 120 in an activated position. The device 120 includes a handle body 126, a needle actuator 128, a stylet knob 130 and a Luer component 132. The handle body 126 is attached to a proximal end of a sheath 134. The needle actuator 128 includes a shaft portion 136 coupled to a handle portion 138. The needle actuator 128 receives and is attached to a proximal end of a needle 140. The stylet knob 130 is attached to a proximal end of a stylet 146. The stylet knob 130 rotatably attaches to a proximal end of the Luer component 132. A distal end of the Luer component 132 is attached to the handle portion 138 of the needle actuator 128.

In the deactivated position, the distal end of the needle 140 is retracted within the sheath 134 (FIG. 4-3). In the activated position, the distal end of the needle 140 is exposed beyond the distal end of the sheath 134 (FIG. 4-2).

As shown in FIG. 4-3, the shaft portion 136 is slidably received within a cavity (i.e., lumen) of the handle body 126. At a proximal end of the cavity of the handle body 126 is an annular groove 152 that receives at least a portion of an O-ring 150. The O-ring 150 keeps the shaft portion 136 from being easily removed from the handle body 126. Interactive operation of the parts of the device 120 are described in more detail below.

Figure 5:
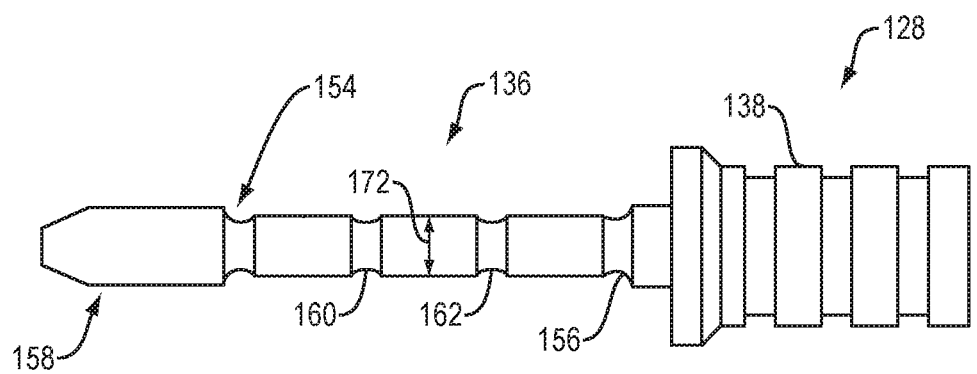
FIG. 5 illustrates a side view of a needle actuator of the aspiration device of FIG. 4-1 in accordance with principles of the present invention.

As shown in FIG. 5, the shaft portion 136 of the needle actuator 128 includes multiple annular grooves 154, 156, 160, 162. As part of assembly, the shaft portion 136 is inserted into the cavity of the handle body 126. A distal section that is distal from the most distal annular groove 154 is forced past the O-ring 150 (FIG. 4-3) until the O-ring 150 becomes seated within the distal annular groove 154. At this position, the device 120 is ready for operation with the distal end of the needle 140 being proximal to the distal end of the sheath 134. The O-ring 150 prevents the distal section 158 of the needle actuator 128 from being completely pulled out of the handle body 126 with an ordinary human-generated force.

A user initiates needle activation by applying a distal force on the handle portion 138 of the needle actuator 128 thus causing the distal annular groove 154 to unseat from the O-ring 150 and slide along the shaft portion 136 until the O-ring 150 audibly and/or tactilely 'pops' into place at the second most distal annular groove 160. When the O-ring 150 seats within the second most distal annular groove 160, the user knows the location of the tip of the needle 140 relative to the sheath 134 without the need to visualize it. Further application of a distal force unseats the O-ring 150 from the second most distal annular groove 160. After the unseating, the O-ring 150 slides along shaft portion 136 until the O-ring 150 audibly and/or tactilely 'pops' into place at the second most proximal annular groove 162. When the O-ring 150 seats within the second most proximal annular groove 162, the user knows the location of the tip of the needle 140 relative to the sheath 134 without the need to visualize it. Further application of a distal force unseats the O-ring 150 from the second most proximal annular groove 162. After the unseating, the O-ring 150 slides along shaft portion 136 until the O-ring 150 seats within the most proximal annular groove 156, at which point the needle 140 is at its fully extended position from the sheath 134. When the O-ring 150 is seated into the most proximal annular groove 156, the needle actuator 128 is maintained in a fully distal position (i.e., fully actuated).

In one embodiment, a first one of the annular grooves 154, 156, 160, 162 includes a physical feature (e.g., groove, bump, altered angle of the surface, etc.) that would produce a unique audibly and/or tactilely pop as the O-ring 150 seats or unseats from the respective groove. If different ones of the annular grooves 154, 156, 160, 162 include different physical features, then the physician is experiencing different audibly and/or tactilely feedback as the needle actuator 128 is advance from one groove to the next. Thus, with minimal training the physician will know the exact position of the needle actuator 128 relative to the handle body 126 and thus the distance the needle 140 is extending beyond the sheath 134.

The shaft portion 136 may be implemented with more or less than four annular grooves.

In one embodiment, the distal annular groove 154 is slightly deeper than the other annular grooves 156, 160, 162. This helps to keep the needle 140 locked in a retracted position until a physician initiated activation occurs. Also, the most distal annular groove 154 may be flanked distally by a wider section of the shaft portion 136. The wider section makes greater contact with the O-ring 150, thus requiring a greater activation force and preventing the needle actuator 128 from being completely pulled out from the handle body 126 without extraordinary force.

In one embodiment, the annular grooves 154, 156, 160, 162 are equally spaced on the shaft portion 136. For example, the spacing may be between 0.5 mm-4 cm. Also, the distances between the annular grooves 154, 156, 160, 162 may be of varying values. The distances may increase, decrease, or alternate in size.

A. A medical device having a needle having a distal end and a proximal end; a needle actuator having an actuator section located at a proximal end of the needle actuator; a shaft section having a distal end and a proximal end, the proximal end of the shaft section being connected to the actuator section, the shaft section comprising at least three annular grooves; and a lumen located within one of the actuator section or the shaft section, the lumen configured to securably receive the proximal end of the needle; a sheath having a distal end and a proximal end, the sheath comprises a lumen configured to receive the needle; and a handle body having a distal end and a proximal end, the distal end of the handle body being coupled to the proximal end of the sheath, the handle body includes a lumen; an annular groove within the lumen of the handle body; and an O-ring at least partially received by the annular groove of the handle body, wherein the at least three annular grooves allow the O-ring to at least partially seat when the respective annular groove is collocated with the annular groove within the lumen of the handle body.

B. The medical device of A, wherein the shaft section including a first section having a first outer diameter value; and a second section having a second outer diameter value, the first outer diameter value is greater than the second outer diameter value, wherein an inner diameter of the O-ring is less than the first outer diameter value.

C. The medical device of A, wherein the at least three annular grooves are spaced equally along the shaft section.

D. The medical device of A, wherein a most distal one of the annular grooves has a depth value that is greater than a depth value of the other annular grooves.

E. The medical device of A, wherein when the O-ring is seated within a most distal one of the annular grooves, the medical device is in a deactivated state.

F. The medical device of E, wherein the deactivated state comprises the distal end of the needle being housed within the sheath.

G. The medical device of A, wherein when the O-ring is seated within any of the annular grooves except the most distal one of the annular grooves, the medical device is in an activated state.

H. The medical device of G, wherein the activated state comprises the distal end of the needle protruding from the distal end of the sheath.

I. The medical device of A, wherein when the O-ring because seated into or gets unseated from one of the annular grooves, at least one of an audible sound or a tactile sensation is produced.

J. The medical device of A, wherein a first one of the grooves comprises one or more first physical features configured to produce at least one of a first audible sound or a first tactile sensation as the O-ring seats within or unseats from the first one of the grooves, wherein a second one of the grooves comprises one or more second physical features configured to produce at least one of a second audible sound or a second tactile sensation as the O-ring seats within or unseats from the second one of the grooves.

K. The medical device of J, wherein the first audible sound or the first tactile sensation are different than the second audible sound or the second tactile sensation.

The description of the invention is merely exemplary in nature and variations that do not depart from the gist of the invention are intended to be within the scope of the invention. Such variations are not to be regarded as a departure from the spirit and scope of the invention.

What is claimed is:

1. A medical device comprising:
a needle having a distal end and a proximal end;
a needle actuator comprising:
   an actuator section located at a proximal end of the needle actuator;
   a shaft section having a distal end and a proximal end, the proximal end of the shaft section being connected to the actuator section, the shaft section comprising:
      a distal section;
      a middle section; and
      at least two annular grooves, wherein a most distal one of the at least two annular grooves is located between the distal section and the middle section and the other one of the at least two annular grooves is located proximally of the middle section; and
   a lumen located within one of the actuator section or the shaft section, the lumen configured to securably receive the proximal end of the needle;
a sheath having a distal end and a proximal end, the sheath comprises a lumen configured to receive the needle; and
a handle body having a distal end and a proximal end, the distal end of the handle body being coupled to the proximal end of the sheath, the handle body comprises:
   a lumen;
   an annular groove within the lumen of the handle body; and an O-ring at least partially received by the annular groove of the handle body, wherein the at least two annular grooves allow the O-ring to at least partially seat when the respective annular groove is collocated with the annular groove within the lumen of the handle body, wherein the middle section of the shaft section comprises a portion having an outside diameter that transitions distally from a first outside diameter value to a second outside diameter value, the second outside diameter value is greater than the first outside diameter value, wherein the most distal one of the annular grooves has a depth value that is greater than a depth value of the other annular grooves.

2. The medical device of claim 1, wherein the distal section has a third outside diameter value, wherein an inner diameter of the O-ring is less than the third outside diameter value.

3. The medical device of claim 1, wherein the at least two annular grooves are spaced equally along the shaft section.

4. The medical device of claim 1, wherein when the O-ring is seated within the most distal one of the annular grooves, the medical device is in a deactivated state.

5. The medical device of claim 4, wherein the deactivated state comprises the distal end of the needle being housed within the sheath.

6. The medical device of claim 1, wherein when the O-ring is seated within any of the two or more annular grooves except the most distal one of the annular grooves, the medical device is in an activated state.

7. The medical device of claim 6, wherein the activated state comprises the distal end of the needle protruding from the distal end of the sheath.

8. The medical device of claim 1, wherein when the O-ring becomes seated into or gets unseated from one of the annular grooves, at least one of an audible sound or a tactile sensation is produced.

9. The medical device of claim 1, wherein when the O-ring becomes seated into or gets unseated from one of the annular grooves, an audible sound and a tactile sensation are produced.

10. The medical device of claim 1, wherein the most distal one of the two or more annular grooves comprises one or more first physical features configured to produce at least one of a first audible sound or a first tactile sensation as the O-ring seats within or unseats from the most distal one of the two or more annular grooves, wherein the other one of the two or more annular grooves comprises one or more second physical features configured to produce at least one of a second audible sound or a second tactile sensation as the O-ring seats within or unseats from the other one of the two or more annular grooves.

11. The medical device of claim 10, wherein the first audible sound or the first tactile sensation are different than the second audible sound or the second tactile sensation.

12. The medical device of claim 10, wherein the first audible sound and the first tactile sensation are different than the second audible sound and the second tactile sensation.

* * * * *

UNITED STATES PATENT AND TRADEMARK OFFICE
CERTIFICATE OF CORRECTION

| | | |
|---|---|---|
| PATENT NO. | : 11,039,819 B2 | Page 1 of 1 |
| APPLICATION NO. | : 15/693070 | |
| DATED | : June 22, 2021 | |
| INVENTOR(S) | : Hugo X. Gonzalez, Madeline C. Graham and Matthew E. Nickeson | |

It is certified that error appears in the above-identified patent and that said Letters Patent is hereby corrected as shown below:

On the Title Page

Item (12) should read:
Gonzalez et al.

Column 1, Item (72) Inventor(s):
Please add the following inventors:
-- Madeline C. Graham -- Redmond, WA
Matthew E. Nickeson -- Redmond, WA --

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*